(12) United States Patent
Matsuyama

(10) Patent No.: US 8,734,721 B2
(45) Date of Patent: May 27, 2014

(54) ANALYZER

(75) Inventor: Shinya Matsuyama, Shizuoka-ken (JP)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 12/730,996

(22) Filed: Mar. 24, 2010

(65) Prior Publication Data

US 2010/0178205 A1 Jul. 15, 2010

Related U.S. Application Data

(63) Continuation of application No. PCT/JP2008/064851, filed on Aug. 20, 2008.

(30) Foreign Application Priority Data

Sep. 26, 2007 (JP) ................................. 2007-249968

(51) Int. Cl.
| | | |
|---|---|---|
| G01N 33/00 | (2006.01) | |
| E03B 11/16 | (2006.01) | |
| E03B 11/00 | (2006.01) | |
| F04B 49/00 | (2006.01) | |
| B08B 6/00 | (2006.01) | |
| B08B 3/04 | (2006.01) | |
| B01D 21/30 | (2006.01) | |

(52) U.S. Cl.
USPC ............... 422/68.1; 422/63; 422/64; 422/65; 134/186; 134/104.1; 134/184; 137/565.01; 137/565.11; 137/565.15; 137/571; 137/572

(58) Field of Classification Search
USPC .......................... 134/18, 56 R, 186, 50, 104.1
See application file for complete search history.

(56) References Cited

U.S. PATENT DOCUMENTS 3,884,265 A * 5/1975 Fry et al. .................. 137/565.16
5,184,634 A * 2/1993 Kitajima ...................... 134/95.1
(Continued)

FOREIGN PATENT DOCUMENTS

EP 0 535 612 A1 4/1993
JP 63-138233 A 6/1988
(Continued)

OTHER PUBLICATIONS

International Search Report from PCT/JP2008/064851, dated Oct. 21, 2008, includes English Translation (2 pages).

(Continued)

*Primary Examiner* — Dirk Bass
*Assistant Examiner* — Jennifer Wecker
(74) *Attorney, Agent, or Firm* — Kilpatrick Townsend & Stockton LLP

(57) ABSTRACT

An analyzer includes, as a cleaning system, a cleanser tank that contains a cleanser; a cleaning-water tank that contains cleaning water; a connection pipe that connects the cleanser tank with the cleaning-water tank; a pump that is provided to the connection pipe and pumps the cleanser out of the cleanser tank to the cleaning-water tank; a valve that is provided to the connection pipe and adjusts a flow of the cleanser from the cleanser tank into the cleaning-water tank; and a control unit that opens the valve and causes the pump to pump the cleanser out of the cleanser tank to the cleaning-water tank via the connection pipe to clean the inside of the cleaning-water tank and the insides of cleaning-water flow-path constituents that form a flow path through which the cleaning water flows from the cleaning-water tank when the specimen is subjected to an analysis process.

3 Claims, 11 Drawing Sheets

(56) References Cited

U.S. PATENT DOCUMENTS

| | | | |
|---|---|---|---|
| 5,827,744 A | 10/1998 | Fose et al. | |
| 6,752,960 B1 * | 6/2004 | Matsubara et al. | 422/63 |
| 7,900,640 B2 | 3/2011 | Eshima | |
| 2005/0129576 A1 * | 6/2005 | Oonuma | 422/64 |
| 2005/0199275 A1 * | 9/2005 | Abbott | 134/56 R |
| 2006/0054190 A1 | 3/2006 | Gifford et al. | |
| 2006/0293200 A1 | 12/2006 | Takayama et al. | |
| 2008/0099057 A1 * | 5/2008 | Dunfee et al. | 134/94.1 |
| 2008/0236301 A1 * | 10/2008 | Fukushima et al. | 73/863 |
| 2009/0120466 A1 * | 5/2009 | Eshima | 134/36 |
| 2009/0133512 A1 * | 5/2009 | Kuroda | 73/863.01 |

FOREIGN PATENT DOCUMENTS

| | | | | | |
|---|---|---|---|---|---|
| JP | 63138233 A | * | 6/1988 | | G01N 1/00 |
| JP | 06-258329 A | | 9/1994 | | |
| JP | 08-105901 A | | 4/1996 | | |
| JP | 2001-041963 A | | 2/2001 | | |
| JP | 2001-091520 A | | 4/2001 | | |
| WO | 2007/004485 A1 | | 1/2007 | | |

OTHER PUBLICATIONS

Chinese Office Action for CN Application No. 200880109379.2, dated May 30, 2012, 3 pages in Chinese only.

European Search Report mailed on Mar. 6, 2013 for EP Patent Application No. 08792572.3, 7 pages.

* cited by examiner

ANALYZER

CROSS-REFERENCE TO RELATED APPLICATIONS

This application is a continuation of PCT international application Ser. No. PCT/JP2008/064851 filed on Aug. 20, 2008 which designates the United States, incorporated herein by reference, and which claims the benefit of priority from Japanese Patent Applications No. 2007-249968, filed on Sep. 26, 2007, incorporated herein by reference.

BACKGROUND OF THE INVENTION

1. Field of the Invention

The present invention relates to an analyzer that includes a cleaning system inside the analyzer for cleaning a specimen that is a target to be analyzed, or a member that has been in contact with liquid that is used for an analyzing process.

2. Description of the Related Art

Analyzers, which can analyze many samples, such as blood or urine, simultaneously and can analyze various ingredients at a high speed with a high accuracy, have been used in various testing fields, such as immunological tests, biochemical tests, and blood transfusion tests (see, for example, Japanese Laid-open Patent Publication No. 08-105901). The samples, i.e., the targets to be analyzed by such an analyzer, are biological fluid materials, for example, blood or urine of a patient, and results of the analysis are used to determine a diagnosis of the condition and a treatment policy for the patient. Therefore, high reliability of the results of the analysis and a short analyzing time taken to obtain the results are demanded. To meet these demands, a typical analyzer includes a cleaning system inside the analyzer for cleaning a sample that is to be analyzed, or a member that has been in contact with liquid that is used in an analyzing process so as to promptly perform the next analyzing process.

If water stains have accumulated inside a cleaning-water tank and pipes through which cleaning water flows, it is impossible to maintain the accuracy of analysis data; therefore, it is necessary to periodically clean the cleaning-water tank and the pipes through which the cleaning water flows so that the water stains cannot accumulate. In a conventional analyzer, pipes through which a cleanser flows from a cleanser tank are completely separated from the pipes through which the cleaning water flows from the cleaning-water tank so that the cleanser and the cleaning water cannot mix together. Therefore, to clean the inside of the cleaning-water tank and the insides of the pipes through which cleaning water flows, a person in charge of maintenance of the analyzer has to perform a complicated cleaning procedure involving the removal of the cleaning-water tank and the pipes through which cleaning water flows from the complicated pipe structure of the analyzer and manual cleaning of them using a cleanser.

SUMMARY OF THE INVENTION

An analyzer according to an aspect of the present invention includes a cleaning system that cleans a specimen to be analyzed or a member that has been in contact with liquid used in an analysis process. The analyzer includes a cleanser tank that contains a cleanser; a cleaning-water tank that contains cleaning water; a connection pipe that connects the cleanser tank with the cleaning-water tank; a pump that is provided to the connection pipe and pumps the cleanser out of the cleanser tank to the cleaning-water tank; a valve that is provided to the connection pipe and adjusts a flow of the cleanser from the cleanser tank into the cleaning-water tank; and a control unit that opens the valve and causes the pump to pump the cleanser out of the cleanser tank to the cleaning-water tank via the connection pipe to clean the inside of the cleaning-water tank and the insides of cleaning-water flow-path constituents that form a flow path through which the cleaning water flows from the cleaning-water tank when the specimen is subjected to an analysis process.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
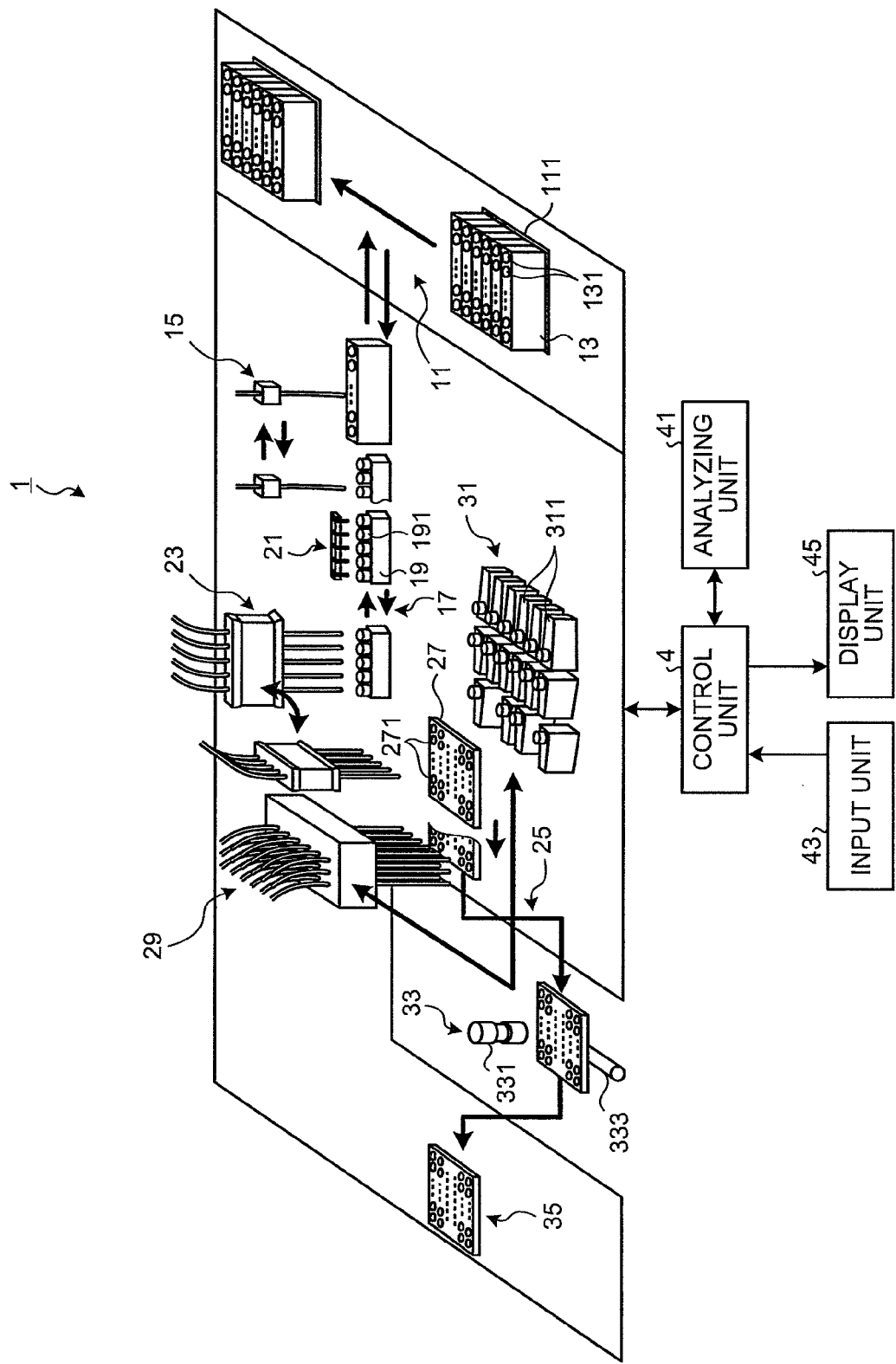
FIG. 1 is a schematic perspective view of an example of the inner configuration of an analyzer 1 according to an embodiment.

An analyzer that analyzes samples that are liquid specimens, such as blood, according to exemplary embodiments of the present invention are described in detail below with reference to the accompanying drawings. The present invention is not limited to these exemplary embodiments. The same parts are denoted with the same reference numerals in the drawings.

FIG. 1 is a schematic perspective view of an example of the inner configuration of an analyzer 1 according to the present embodiment. The analyzer 1 is a device that conducts immunological tests concerning, for example, an antigen-antibody reaction of blood to be tested using immunological agglutination behavior. The analyzer 1 includes a sample-rack conveying unit 11, a sample dispensing unit 15, a diluted-sample-rack conveying unit 17, a diluting-solution dispensing unit 21, a diluted-sample dispensing unit 23, a plate conveying unit 25, a reagent dispensing unit 29, a reagent storage unit 31, a measurement unit 33, and a plate collecting unit 35.

The sample-rack conveying unit 11 conveys, under the control of a later-described control unit 4, sample racks 13 that are arranged on a rack feeder 111. A plurality of sample vessels 131 containing samples (specimens) is mounted on the sample rack 13. The sample-rack conveying unit 11 sequentially conveys the sample racks 13 to a position where the sample vessel 131 is in a predetermined sample suction position. The sample contained in the sample vessel 131 that is conveyed to the sample suction position is dispensed to a plurality of diluted sample vessels 191 by the sample dispensing unit 15.

The sample dispensing unit 15 includes a nozzle through which the samples are suck and discharged. Under the control of the control unit 4, the sample dispensing unit 15 sucks, when the sample vessel 131 is conveyed to the sample suction position, the sample from the sample vessel 131 using the nozzle and then conveys the sample to a predetermined sample discharge position. A diluted sample rack 19 on which the plural diluted sample vessels 191 are mounted is arranged at the sample discharge position. The sample dispensing unit 15 sequentially discharges the sucked sample to each of the diluted sample vessels 191, thus performing the dispensation.

The diluted-sample-rack conveying unit 17 conveys, under the control of the control unit 4, the diluted sample rack 19 to a predetermined diluting-solution dispensing position and then conveys it to a predetermined diluted-sample suction position. When the diluted sample rack 19 is conveyed to the diluting-solution dispensing position, diluting solution is dispensed to each of the diluted sample vessels 191 on the diluted sample rack 19 by the diluting-solution dispensing unit 21. After that, when the diluted sample rack 19 is conveyed to the diluted-sample suction position, the diluted samples are conveyed from the diluted sample vessels 191 on the diluted sample rack 19 to a predetermined diluted-sample discharge position by the diluted-sample dispensing unit 23.

The diluting-solution dispensing unit 21 includes a plurality of nozzles through which the diluting solution is discharged. When the diluted sample rack 19 is conveyed to the diluting-solution dispensing position, the diluting-solution dispensing unit 21 dispenses a predetermined amount of the diluting solution to each of the diluted sample vessels 191 on the diluted sample rack 19 using the nozzles.

The diluted-sample dispensing unit 23 includes a plurality of sample nozzles through which the diluted samples are suck and discharged. Under the control of the control unit 4, the diluted-sample dispensing unit 23 sucks, when the diluted sample rack 19 is conveyed to the diluted-sample suck position, the diluted sample from each of the diluted sample vessels 191 on the diluted sample rack 19 using the corresponding sample nozzle and conveys the diluted samples to the diluted-sample discharge position. A microplate 27 formed with a plurality of reaction vessels 271, which are called "wells", arranged in a matrix pattern is arranged at the diluted-sample discharge position. The diluted-sample dispensing unit 23 dispenses each of the diluted samples to each of the reaction vessels 271, thus performing the dispensation.

To dispense the diluted sample and a reagent to each of the reaction vessels 271 of the microplate 27 and measure the compound liquid of the diluted sample and the reagent contained in each of the reaction vessels 271, the plate conveying unit 25 conveys, under the control of the control unit 4, the microplate 27 from the diluted-sample discharge position to a position where the reaction vessels 271 are in a reagent discharge position, and then conveys it to a measurement position. When the reaction vessels 271 are conveyed to the reagent discharge position, the reagent is dispensed to the reaction vessels 271 by the reagent dispensing unit 29.

The reagent dispensing unit 29 includes reagent nozzles through which the reagent is suck and discharged. The reagent dispensing unit 29 sucks, under the control of the control unit 4, the reagent from each of reagent vessels 311 contained in the reagent storage unit 31 using the reagent nozzles, conveys the reagent to the reagent discharge position, and discharges the reagent to each of the reaction vessels 271 of the microplate 27 that is conveyed by the plate conveying unit 25 to the reagent discharge position. The reagent storage unit 31 stores therein the plural reagent vessels 311 each containing a predetermined reagent that causes an antigen-antibody reaction with the samples.

The diluted sample is dispensed to each of the reaction vessels 271 of the microplate 27 by the diluted-sample dispensing unit 23 and the reagent is dispensed to each of the reaction vessels 271 by the reagent dispensing unit 29. When a period required for the reaction has passed and the antigen-antibody reaction with the samples contained in the reaction vessels 271 is completed, the microplate 27 is conveyed to the measurement position by the plate conveying unit 25. An agglutination reaction pattern is formed on the bottom surface of each of the reaction vessels 271 as the effect of the antigen-antibody reaction.

The measurement unit 33 includes an imaging unit 331, such as a CCD camera, that is arranged above the measurement position and takes an image of the microplate 27 that is in the measurement position from the upper position; and a light source 333 that is arranged under the measurement position and illuminates each of the reaction vessels 271 of the microplate 27 with an illumination light from the lower position. The imaging unit 331 takes an image of the agglutination reaction pattern that is formed on the bottom surface of each of the reaction vessels 271 by receiving an amount of light having passed through the reaction vessel 271. The obtained measurement result (image data) is output to the control unit 4. It is noted in general that a positive sample induces formation of the agglutination as a reaction of the sample to the reagent while a negative sample does not induce formation of the agglutination.

The plate collecting unit 35 collects the microplate 27 after the measurement by the measurement unit 33 is completed. The collected microplate 27 is cleaned by a cleaning unit (not shown) for reuse. More particularly, the compound liquid is drained from each of the reaction vessels 271 and the reaction vessels 271 are cleaned by discharging and sucking of cleaning solution, such as cleanser and cleaning water. The microplate 27 can be destroyed at the end of only one measurement depending on contents of the test.

The analyzer 1 includes the control unit 4 that integrally controls operations of the device by controlling operating timing of the units that form the device and sending data to the units. The control unit 4 is formed with a micro computer or the like that includes a built-in memory that stores therein various data including results of the analysis and data required for operations of the analyzer 1. The control unit 4 is arranged at an appropriate location inside the device. The control unit 4 is connected to an analyzing unit 41 and outputs the measurement result obtained by the measurement unit 33 to the analyzing unit 41. The analyzing unit 41 analyzes the antigen-antibody reaction using the measurement result obtained by the measurement unit 33 and outputs an analysis result to the control unit 4. For example, the analyzing unit 41 processes the image data obtained by the measurement unit 33 and detects/determines the agglutination reaction pattern formed on the bottom surface of each of the reaction vessels 271. The control unit 4 is connected to an input unit 43 formed with an input device, such as a keyboard or a mouse, that is used to input information required for the analysis, such as the number of samples and analysis items. The control unit 4 is connected to a display unit 45 formed with a display device, such as an LCD and an ELD, that displays thereon various screens including an analysis result screen, a warning screen, and an input screen for inputting various settings.

Figure 2:
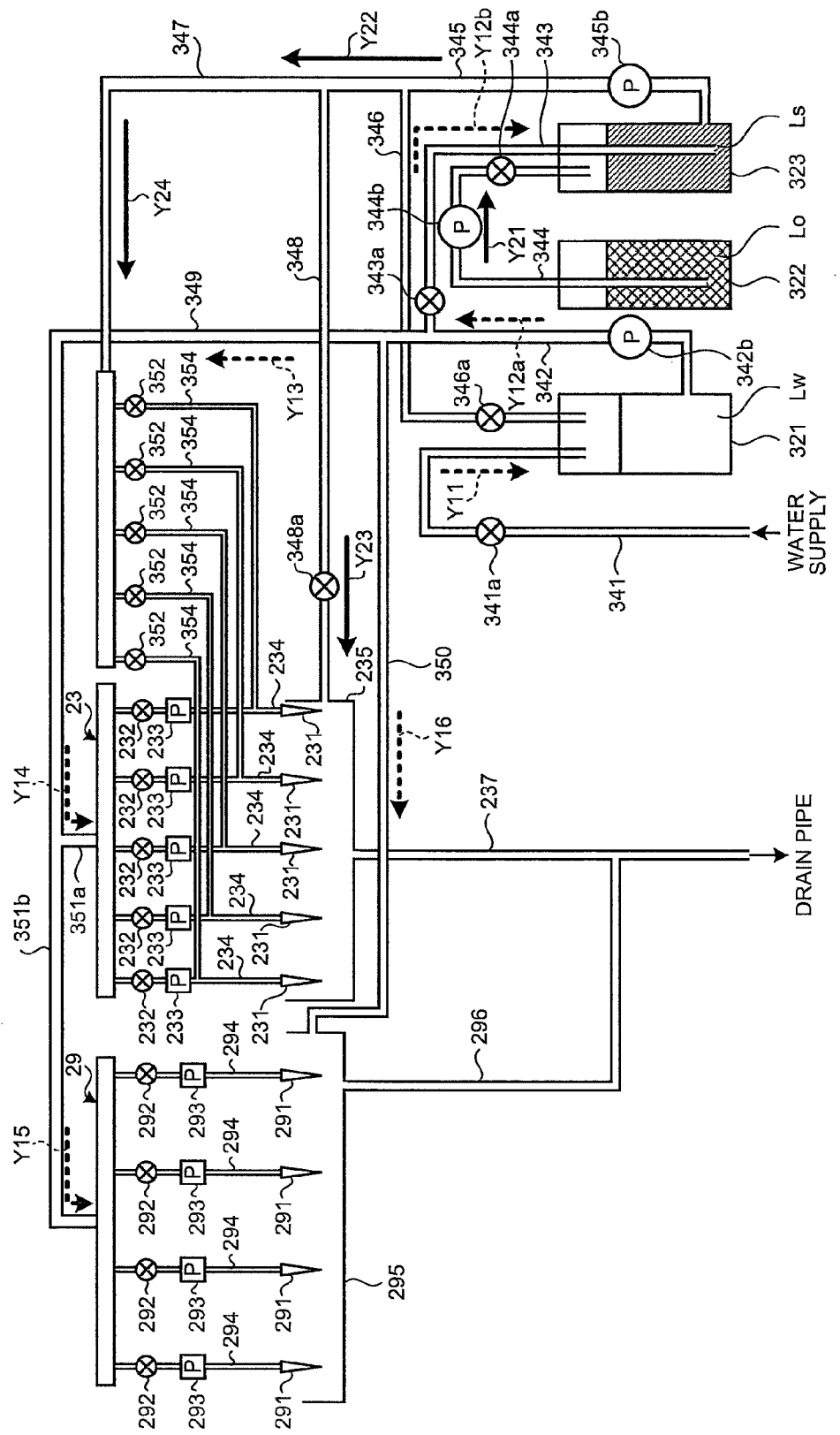
FIG. 2 is a schematic diagram that explains a cleaning system for cleaning, inside the device, a sample to be analyzed by the analyzer shown in FIG. 1 or a member that has been in contact with liquid that is used for an analysis process.

A cleaning system that cleans the samples that are targets to be analyzed, and members that have been in contact with liquid that is used for the analysis process is described below with reference to FIG. 2. As shown in FIG. 2, the analyzer 1 shown in FIG. 1 includes, as the cleaning system, a cleaning-water tank 321 that contains cleaning water Lw, an undiluted-cleanser tank 322 that contains undiluted cleanser Lo, and a cleanser tank 323 that contains cleanser Ls that is diluted to a predetermined concentration.

The cleaning water Lw is purified water including any one of or combinations of ion-exchange water, distilled water, and ultra-filtrated water. When a valve 341a provided to a pipe 341 opens under the control of the control unit 4, the cleaning water Lw is supplied from a cleaning-water supply source to the cleaning-water tank 321 via the pipe 341 as indicated by an arrow Y11.

The cleaning-water tank 321 is connected to a pipe 342 through which the cleaning water Lw flows and a pipe 343 that is connected to the cleanser tank 323 is bifurcated from the pipe 342. The pipe 342 is provided with a pump 342b so that the cleaning water is pumped out of the cleaning-water tank 321. The pipe 343 is provided with a valve 343a. When the valve 343a opens and the pump 342b turns activated under the control of the control unit 4, the cleaning water Lw is supplied from the cleaning-water tank 321 to the cleanser tank 323 as indicated by an arrow Y12a and an arrow Y12b.

A pipe 350 that is connected to a reagent-nozzle cleaning tank 295, in which each of reagent nozzles 291 is cleaned after the reagent dispensation, is bifurcated from the pipe 342. When the valve 343a closes and the pump 342b turns activated under the control of the control unit 4, the cleaning water Lw is supplied from the cleaning-water tank 321 to the reagent-nozzle cleaning tank 295 via the pipe 350 as indicated by an arrow Y16. It is noted that the cleaning water Lw is drained from the reagent-nozzle cleaning tank 295 through a pipe 296 that is connected to a drain pipe.

A pipe 349 is bifurcated from the pipe 342, and the pipe 349 is bifurcated into a pipe 351b that is connected to each of the reagent nozzles 291 of the reagent dispensing unit 29 and a pipe 351a that is connected to each of sample nozzles 231 of the diluted-sample dispensing unit 23.

The pipe 351b is connected to both each of the reagent nozzles 291 and each of tubes 294 that are provided with valves 292 and syringe pumps 293. When the reagent dispensation is performed under the control of the control unit 4, the valves 292 open and the syringe pumps 293 turn activated. As a result, the cleaning water Lw flows from the cleaning-water tank 321 via the pipes 342, 349, and 351b as indicated by arrows Y13 and Y15 and thereby the reagent nozzles 291 receive pressure required for the reagent dispensation, thus the reagent dispensing process using the reagent nozzles 291 is implemented. The pipe 351a is connected to both each of the sample nozzles 231 and each of tubes 234 that are provided with valves 232 and syringe pumps 233. When the sample dispensation is performed under the control of the control unit 4, the valves 232 open and the syringe pumps 233 turn activated. As a result, the cleaning water Lw flows from the cleaning-water tank 321 via the pipes 342, 349, and 351a as indicated by the arrows Y13 and Y14 and thereby the sample nozzles 231 receive pressure required for the reagent dispensation, thus the sample dispensing process using the sample nozzles 231 is implemented.

The undiluted-cleanser tank 322 is connected to the cleanser tank 323 via a pipe 344. When a valve 344a that is provided to the pipe 344 opens and a pump 344b that is provided to the pipe 344 turns activated under the control of the control unit 4, the undiluted cleanser Lo is supplied from the undiluted-cleanser tank 322 to the cleanser tank 323 as indicated by an arrow Y21. The control unit 4 controls an amount of the cleaning water Lw to be supplied from the cleaning-water tank 321 to the cleanser tank 323 and an amount of the undiluted cleanser Lo to be supplied from the undiluted-cleanser tank 322 to the cleanser tank 323 by controlling open/close operations of the valves 343a and 344a and operations of the pumps 342b and 344b, thereby adjusting the concentration of the cleanser Ls in the cleanser tank 323 to a target value predetermined depending on the object to be cleaned.

A pipe 345 through which the prepared cleanser Ls having the predetermined concentration flows is connected to the cleanser tank 323. The pipe 345 is connected to a pipe 348 that is connected to a sample-nozzle cleaning tank 235, in which the outside of each of the sample nozzles 231 is cleaned after the sample dispensation, and a pipe 347 through which the cleanser Ls is supplied to clean the inside of each of the sample nozzles. When a valve 348a that is provided to the pipe 348 opens and a pump 345b that is provided to the pipe 345 turns activated under the control of the control unit 4, the cleanser Ls is supplied from the cleanser tank 323 to the sample-nozzle cleaning tank 235 via the pipe 348 as indicated by arrows Y22 and Y23. It is noted that the cleanser Ls is drained from the sample-nozzle cleaning tank 235 through a pipe 237 that is connected to the drain pipe.

The pipe 347 is provided with tubes 354 each connected to a corresponding one of the tubes 234. When the valves 232 that are provided to the tubes 234 close, valves 352 that are provided to the tubes 354 open, and the pump 345b turns activated under the control of the control unit 4, the cleanser Ls is supplied from the cleanser tank 323 into the pipes 345 and 347 and each of the tubes 354 and 234 as indicated by arrows Y22 and Y24 so that the insides of the sample nozzles 231 are cleaned with the cleanser Ls.

In the analyzer 1, the cleanser tank 323 and the cleaning-water tank 321 are connected to each other via pipes. More particularly, a connection pipe 346 that is connected to the cleaning-water tank 321 is bifurcated from the pipe 345 through which the cleanser Ls flows from the cleanser tank 323. The connection pipe 346 is provided with a valve 346a that is used to adjust the flow of the cleanser Ls from the cleanser tank 323 to the cleaning-water tank 321. The above-described pump 345b is provided to a connection pipe that connects the cleanser tank 323 with the cleaning-water tank 321 and has a function to send the cleanser Ls from the cleanser tank 323 to the cleaning-water tank 321.

When the valve 346a opens with all the valves other than the valve 346a being closed and the pump 345b that is provided to the pipe 345 turns activated under the control of the control unit 4, the cleanser Ls is pumped out of the cleanser tank 323 by the pump 345b into the cleaning-water tank 321 via the pipe 345 and the connection pipe 346. Thus, the inside of the cleaning-water tank 321 is cleaned with the cleanser Ls that is supplied from the cleanser tank 323 into the cleaning-water tank 321.

When the pump 342b that is provided to the pipe 342 turns activated under the control of the control unit 4 in the above-described situation, the cleanser Ls is supplied from the cleaning-water tank 321 into the cleaning-water flow-path constituents, which form the flow-path through which the cleaning water Lw flows from the cleaning-water tank 321 in the process of analyzing the specimen, including the pipes 342, 349, 350, 351a, and 351b, the reagent-nozzle cleaning tank 295, the tubes 234 and 294, and the reagent nozzles 291. As a result, the insides of the cleaning-water flow-path constituents are cleaned.

Figure 3:
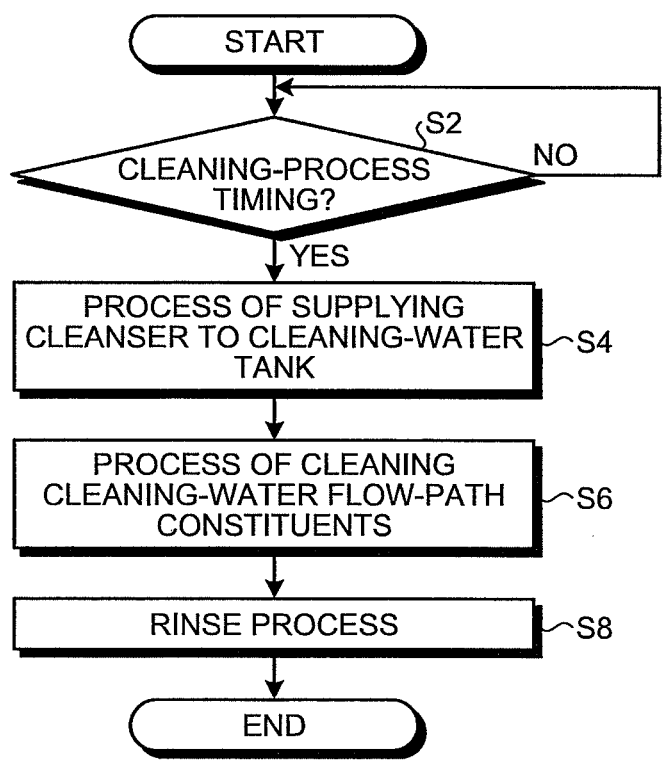
FIG. 3 is a flowchart of a process of cleaning the inside of a cleaning-water tank and the insides of cleaning-water flow-path constituents shown in FIG. 2.

The process of cleaning the inside of the cleaning-water tank 321 and the insides of the cleaning-water flow-path constituents shown in FIG. 2 is described below with reference to FIG. 3. As shown in FIG. 3, the control unit 4 determines whether cleaning-process timing for cleaning the inside of the cleaning-water tank 321 and the insides of the cleaning-water flow-path constituents has come (Step S2).

For example, when the input unit 43 receives information about an instruction to clean the inside of the cleaning-water tank 321 and the insides of the cleaning-water flow-path constituents, and the control unit 4 receives the information about the instruction from the input unit 43, the control unit 4 determines that the cleaning-process timing for cleaning the inside of the cleaning-water tank 321 and the insides of the cleaning-water flow-path constituents has come. Moreover, when a predetermined time period has elapsed after the last cleaning of the inside of the cleaning-water tank 321 and the insides of the cleaning-water flow-path constituents, the control unit 4 determines that the cleaning-process timing for cleaning the inside of the cleaning-water tank 321 and the insides of the cleaning-water flow-path constituents has come. Still moreover, when the number of analysis requests received by the analyzer 1 is a predetermined value or smaller, the control unit 4 determines that the cleaning-process timing for cleaning the inside of the cleaning-water tank 321 and the insides of the cleaning-water flow-path constituents has come. This is, for example, a case of the analyzer 1 being the stand-by status or a case where it is possible to take time to perform the cleaning process for cleaning the inside of the cleaning-water tank 321 and the insides of the cleaning-water flow-path constituents because the number of analysis requests is small. Furthermore, when it is determined using a timer or the like that time has reached a predetermined time set in advance as the cleaning time at which the inside of the cleaning-water tank 321 and the insides of the cleaning-water flow-path constituents are to be cleaned, the control unit 4 determines that the cleaning-process timing for cleaning the inside of the cleaning-water tank 321 and the insides of the cleaning-water flow-path constituents has come.

The control unit 4 repeats the determination process of Step S2 until determining that the cleaning-process timing for cleaning the inside of the cleaning-water tank 321 and the insides of the cleaning-water flow-path constituents has come. If it is determined that the cleaning-process timing for cleaning the inside of the cleaning-water tank 321 and the insides of the cleaning-water flow-path constituents has come (Step S2: Yes), the control unit 4 performs the process of supplying the reagent to the cleaning-water tank 321 to clean the inside of the cleaning-water tank 321, which is a part of the inside of the cleaning-water tank 321 and the insides of the cleaning-water flow-path constituents (Step S4).

Figure 4:
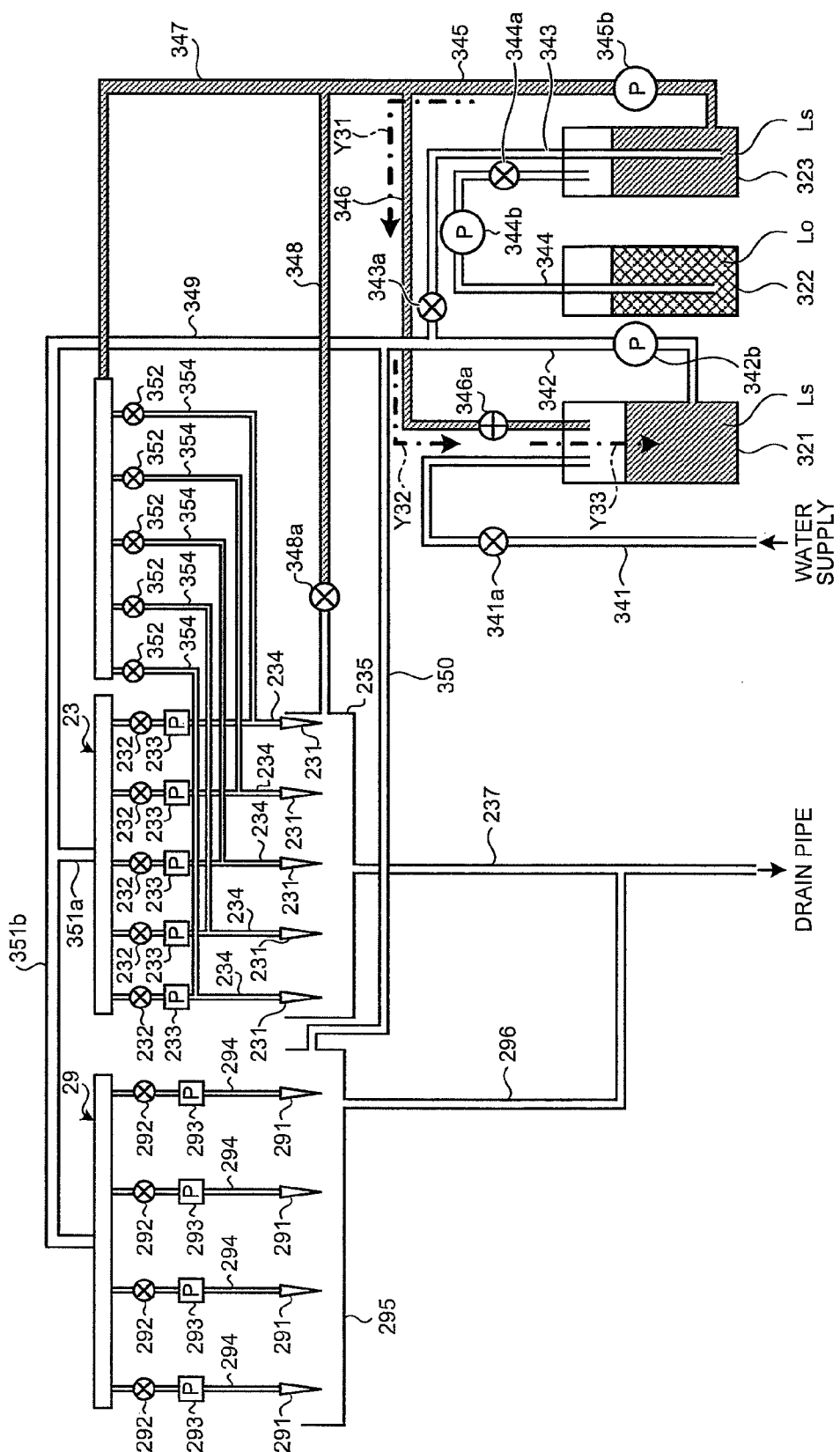
FIG. 4 is a schematic diagram that explains a process of supplying a cleanser to the cleaning-water tank shown in FIG. 3.

The process of supplying the reagent to the cleaning-water tank 321 is described in details below with reference to FIG. 4. As shown in FIG. 4, the control unit 4 opens the valve 346a that is provided to the connection pipe 346 with all the valves other than the valve 346a being closed. The control unit 4 activates the pump 345b of the pipe 345 with all the pumps other than the pump 345b being inactivated. When the valve 346a opens and the pump 345b activates, the prepared cleanser Ls having the predetermined concentration is sent from the cleanser tank 323 to the cleaning-water tank 321 via the pipe 345, the connection pipe 346, and the valve 346a as indicated by arrows Y31, Y32, and Y33. As a result, the cleaning-water tank 321 is filled with the cleanser Ls and therefore the inside of the cleaning-water tank 321 is cleaned with the cleanser Ls. If it is required to change the concentration of the cleanser Ls to appropriately clean the inside of the cleaning-water tank and the insides of the cleaning-water flow-path constituents because, for example, contents of the cleanser is changed, the analyzer has conducted an analysis for a specific analysis item, or an analysis of a particular sample needs an increase of the cleaning effect, the control unit 4 prepares the cleanser Ls having the target concentration by adjusting the open time of the valve 346a and the valve 341a.

After the process of supplying the reagent to the cleaning-water tank 321 is completed, the control unit 4 performs a process of cleaning the cleaning-water flow-path constituents, such as the pipes through which the cleaning water flows and the nozzles that is cleaned with the cleaning water only in normal analysis processes (Step S6).

Figure 5:
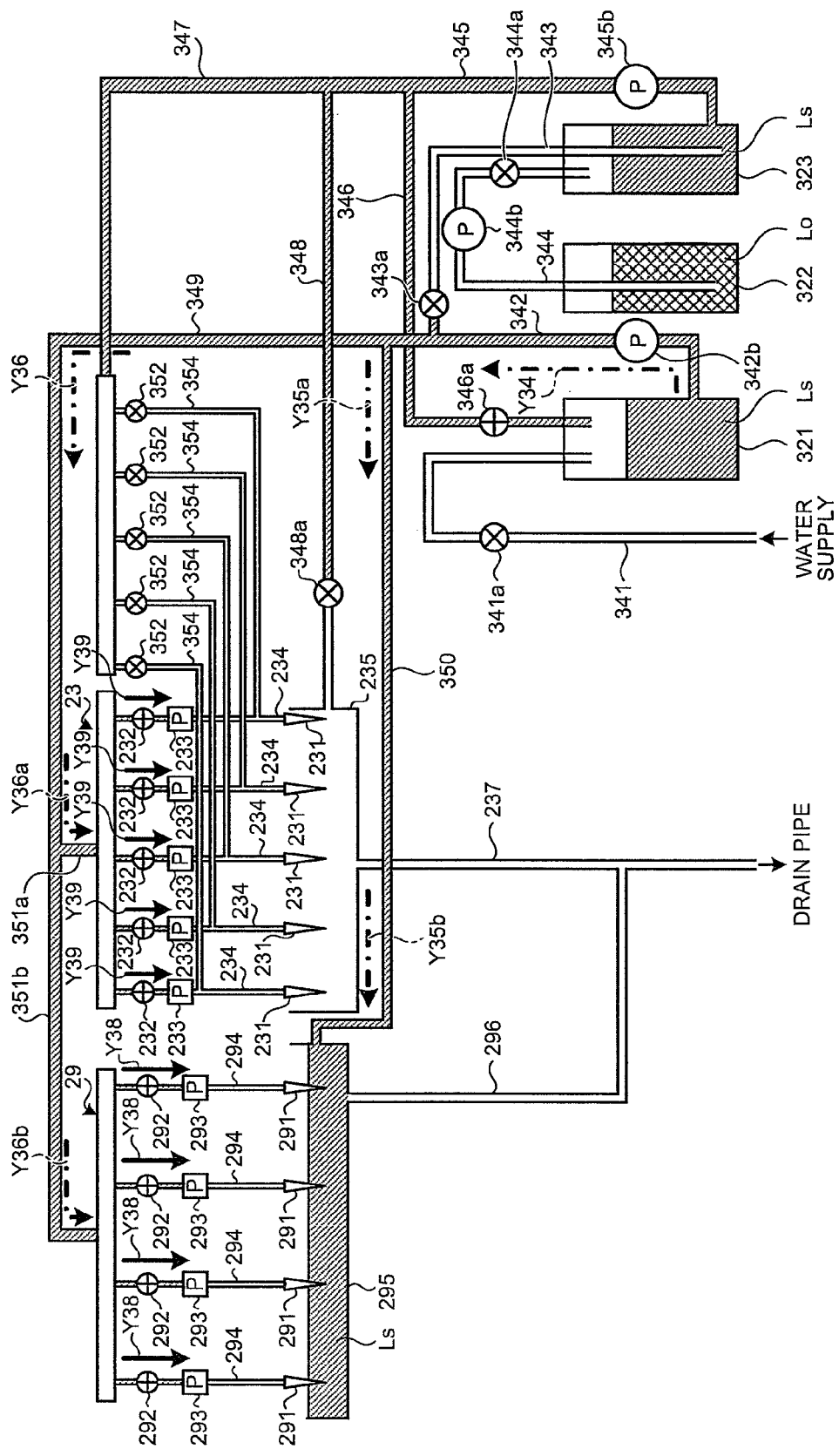
FIG. 5 is a schematic diagram that explains a process of cleaning the cleaning-water flow-path constituents shown in FIG. 3.

The process of cleaning the cleaning-water flow-path constituents is described in details below with reference to FIG. 5. As shown in FIG. 5, the control unit 4 opens the valve 346a with all the valves other than the valve 346a being closed. The control unit 4 then activates both the pump 345b and the pump 342b of the pipe 342. Because the pump 342b activates with the valve 346a open, the cleanser Ls in the cleaning-water tank 321 coming from the cleanser tank 323 flows into the pipe 342 as indicated by an arrow Y34. After passed through the pipe 342, the cleanser Ls flows into the pipe 350 that is bifurcated from the pipe 342 and further flows into the reagent-nozzle cleaning tank 295 as indicated by arrows Y35a and Y35b. The cleanser Ls in the pipe 342 flows into the pipe 349 that is bifurcated from the pipe 342 as indicated by an arrow Y36, and then flows into the pipes 351a and 351b as indicated by arrows Y36a and Y36b. Moreover, when both the valve 232 of the diluted-sample dispensing unit 23 and the valve 292 of the reagent dispensing unit 29 open under the control of the control unit 4, the cleanser Ls flows from the pipes 351a and 351b into the tubes 234 and 294 as indicated by arrows Y38 and Y39. Still moreover, when the syringe pumps 293 of the reagent dispensing unit 29 is driven for the suck/discharge operation under the control of the control unit 4, the cleanser Ls is suck from the reagent-nozzle cleaning tank 295 into the reagent nozzles 291.

In this manner, the cleanser Ls flows from the cleaning-water tank 321 to the cleaning-water flow-path constituents, through which only the cleaning water Lw flows from the cleaning-water tank 321 in the normal analysis process, such as the pipes 342, 349, 350, 351a, and 351b, the reagent-nozzle cleaning tank 295, the tubes 234 and 294, and the reagent nozzles 291 and therefore each of the cleaning-water flow-path constituents is cleaned with the cleanser Ls.

After that, the control unit 4 performs a rinse process of rinsing the inside of the cleaning-water tank 321 and the insides of the cleaning-water flow-path constituents with the cleaning water Lw after cleaning them with the cleanser Ls (Step S8). The rinse process is described in details below with reference to FIG. 6.

Figure 6:
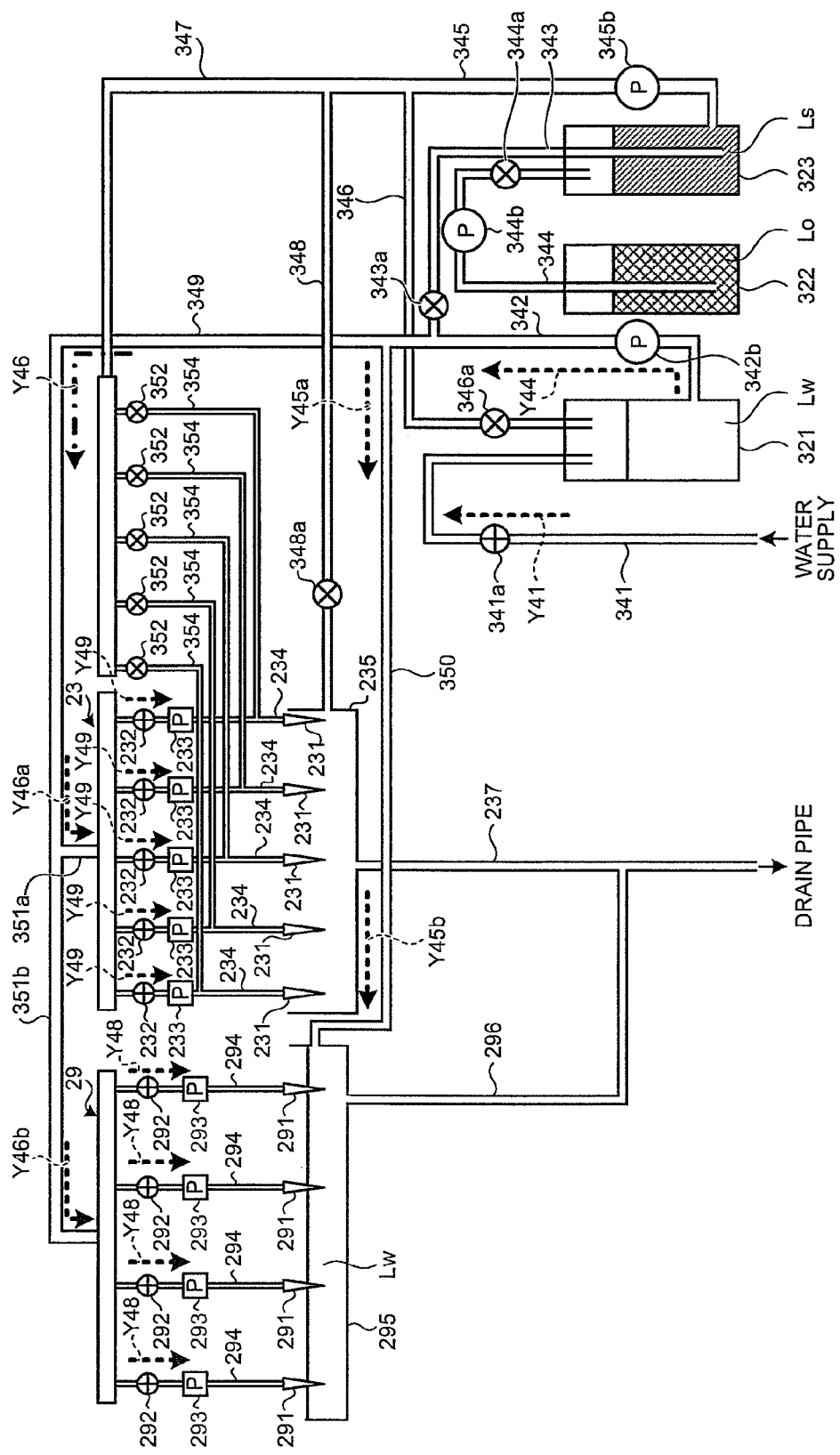
FIG. 6 is a schematic diagram that explains a rinse process shown in FIG. 3.

As shown in FIG. 6, the control unit 4 closes the valve 346a of the connection pipe 346 that connects the cleanser tank 323 with the cleaning-water tank 321 so that the cleanser Ls cannot be supplied into the cleaning-water tank 321 and each of the cleaning-water flow-path constituents, thus stopping supply of the cleanser into the cleaning-water tank 321. After that, to clean the inside of the cleaning-water tank 321 with the cleaning water Lw, the control unit 4 opens the valve 341a of the pipe 341 that is connected to the cleaning-water supply source. As a result, the cleaning water Lw is supplied from the cleaning-water supply source to the cleaning-water tank 321 as indicated by an arrow Y41 and the inside of the cleaning-water tank 321 is rinsed.

To rinse the inside of each of the cleaning-water flow-path constituents, the control unit 4 activates the pump 342b of the pipe 342 and flows the cleaning water Lw from the cleaning-water tank 321 into the pipe 342 as indicated by an arrow Y44. After flowing into the pipe 342, the cleaning water Lw further flows into the pipe 350 and then the reagent-nozzle cleaning tank 295 as indicated by arrows Y45a and Y45b, and therefore the insides of the pipe 350 and the reagent-nozzle cleaning tank 295 are rinsed. After flowing into the pipe 342, the cleaning water Lw flows into the pipes 349, 351a, and 351b as indicated by arrows Y46, Y46a, and Y46b and further flows into the tubes 234 and 294 as indicated by arrows Y48 and Y49 via the valves 232 and 292 that are open under the control of the control unit 4, thus those members are rinsed. After that, the syringe pumps 293 of the reagent dispensing unit 29 are driven for suck/discharge operation under the control of the control unit 4 so that the cleaning water Lw is suck from the reagent-nozzle cleaning tank 295 into the reagent nozzles 291 and thus the reagent nozzles 291 are rinsed. The number of rinses is predetermined depending on the type of the cleanser Ls, the concentration of the cleanser Ls, and the pipe structure. The number of rinses in the analyzer 1 is, for example, three or six.

When the rinse process is completed, the process of cleaning the inside of the cleaning-water tank 321, which contains only the cleaning water Lw in the normal analysis process, and the inside of the cleaning-water flow-path constituents, through which only the cleaning water Lw flows from the cleaning-water tank 321 in the normal analysis process, formed with the pipes 342, 349, 350, 351a, and 351b, the reagent-nozzle cleaning tank 295, the tubes 234 and 294, and the reagent nozzles 291 is completed.

In this manner, the connection pipe 346 that connects the cleanser tank 323 with the cleaning-water tank 321 is provided in the present embodiment. To clean the inside of the cleaning-water tank 321 and the insides of the cleaning-water flow-path constituents, the valve 346a provided to the connection pipe 346 opens and the pump 345b provided to the pipe 345 to which the connection pipe 346 is connected turns activated and thereby the cleanser Ls is sent from the cleanser tank 323 to the cleaning-water tank 321 via the connection pipe 346. Therefore, as for cleaning of the inside of the cleaning-water tank and the inside of the pipes through which the cleaning water flows, the analyzer 1 does not need the complicated cleaning procedure in which the person in charge of maintenance of the analyzer removes the cleaning-water tank and the pipes through which cleaning water flows from the complicated pipe structure of the analyzer and manually clean them using a cleanser. In other words, the analyzer 1 can easily clean the inside of the cleaning-water tank and the insides of the cleaning-water flow-path constituents using the cleanser.

Moreover, in the analyzer 1, when receiving information about the instruction to clean the inside of the cleaning-water tank 321 and the insides of the cleaning-water flow-path constituents from the input unit 43, the control unit 4 opens the valve 346a and causes the pump 345b to pump the cleanser Ls out of the cleanser tank 323 to the cleaning-water tank 321 via the connection pipe 346, thereby cleaning the inside of the cleaning-water tank and the insides of the cleaning-water flow-path constituents. Therefore, in the analyzer 1, the person in charge of maintenance of the analyzer 1 can clean the inside of the cleaning-water tank and the insides of the cleaning-water flow-path constituents just by performing the simple operation, i.e., making an instruction using the input unit 43 to clean the inside of the cleaning-water tank and the insides of the cleaning-water flow-path constituents. In other words, the analyzer 1 can reduce the workload of the maintenance person concerning the maintenance processes compared with that of the conventional analyzer that requires the manual operation to clean the inside of the cleaning-water tank and the insides of the cleaning-water flow-path constituents.

In the analyzer 1, when a predetermined time period has elapsed after the last cleaning of the inside of the cleaning-water tank 321 and the insides of the cleaning-water flow-path constituents, when the number of the analysis requests that has been received by the analyzer 1 is a predetermined number or smaller, or when reaching a predetermined time set in advance as the cleaning time at which the inside of the cleaning-water tank and the insides of the cleaning-water flow-path constituents are due to be cleaned, the control unit 4 opens the valve 346a and causes the pump 345b to pump the cleanser Ls out of the cleanser tank 323 to the cleaning-water tank 321 via the connection pipe 346, thereby cleaning the inside of the cleaning-water tank and the insides of the cleaning-water flow-path constituents. In other words, the analyzer 1 further reduces the workload of the person in charge of maintenance of the analyzer 1 concerning the maintenance processes.

Figure 7:
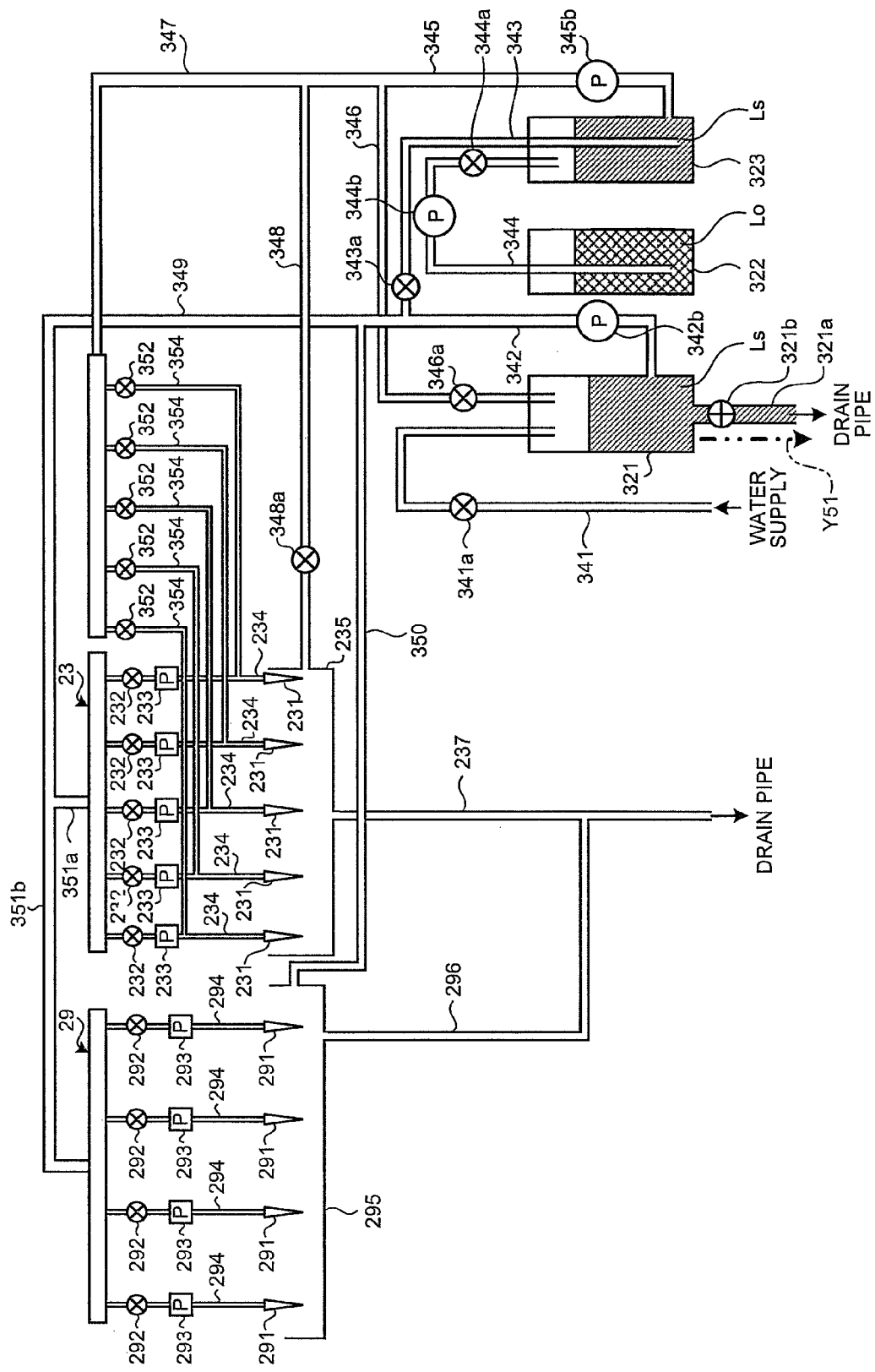
FIG. 7 is a schematic diagram that explains another cleaning system for cleaning, inside the device, a sample to be analyzed by the analyzer shown in FIG. 1 or a member that has been in contact with the liquid that is used for the analysis process.

As shown in FIG. 7, the cleaning-water tank 321 of the analyzer 1 may be connected to a pipe 321a, which is connected to the drain pipe, in such a manner that after the cleanser Ls is supplied to the cleaning-water tank 321 in the process of cleaning the inside of the cleaning-water tank and the insides of the cleaning-water flow-path constituents, the cleanser Ls is drained directly from the cleaning-water tank 321. This makes it possible to reduce time that it takes to clean the inside of the cleaning-water tank and the insides of the cleaning-water flow-path constituents. In the analyzer 1, when a valve 321b that is provided to the pipe 321a opens under the control of the control unit 4, the cleanser Ls is drained from the cleaning-water tank 321 as indicated by an arrow Y51 after the inside of the cleaning-water tank 321 is cleaned. It is noted that the valve 321b is always closed, except when the cleanser Ls is drained from the cleaning-water tank 321, so that the liquid cannot be drained out of the cleaning-water tank 321.

In the present embodiment, the undiluted-cleanser tank 322 is included in the analyzer 1, and the cleanser Ls is prepared inside the analyzer 1 to have the predetermined concentration. However, as shown in FIG. 8, the analyzer 1 may include a cleanser tank 323c that contains the prepared cleanser Ls having the predetermined concentration.

Figure 8:
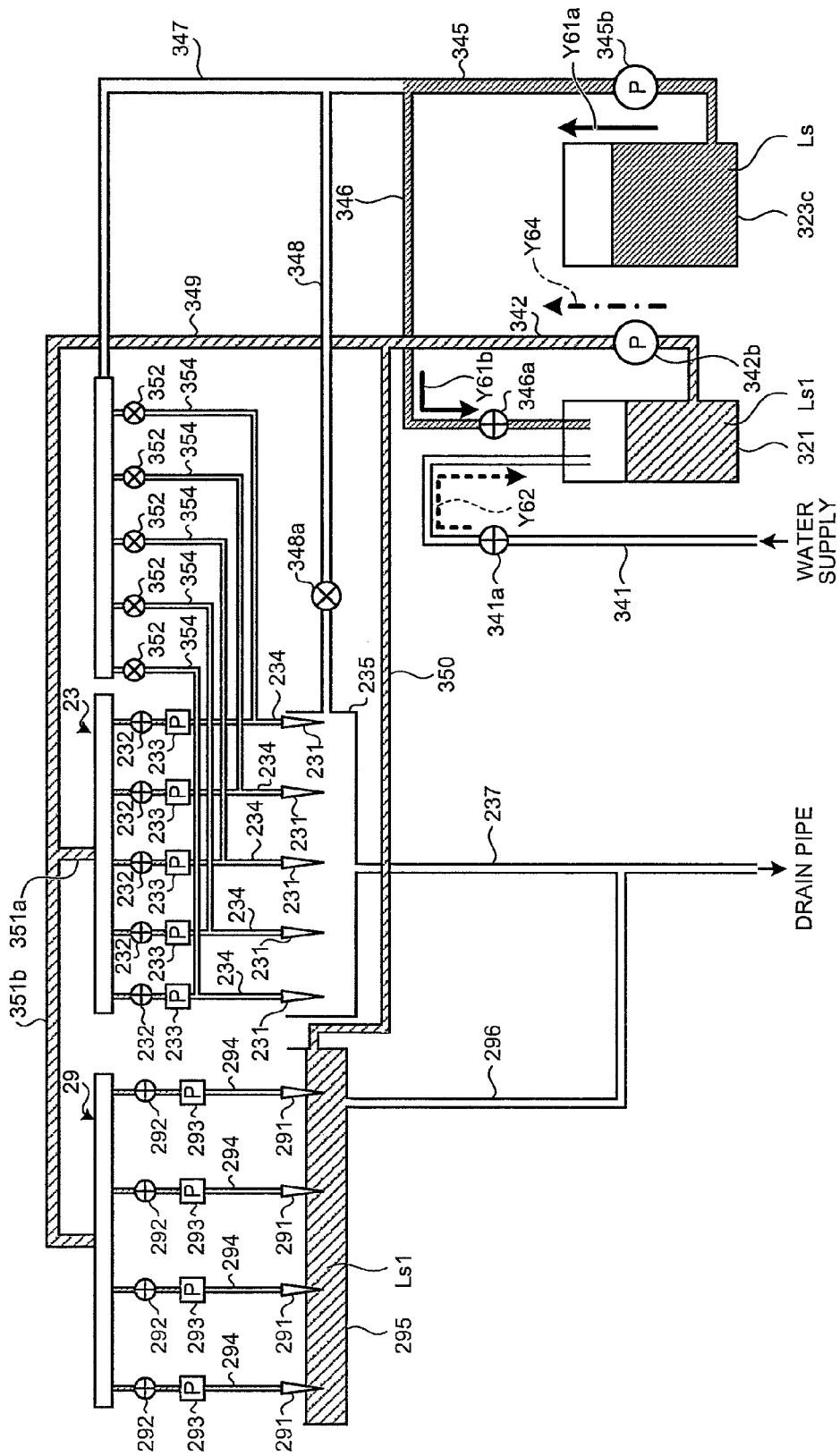
FIG. 8 is a schematic diagram that explains another cleaning system for cleaning, inside the device, a sample to be analyzed by the analyzer shown in FIG. 1 or a member that has been in contact with the liquid that is used for the analysis process.

In this case, as shown in FIG. 8, when the pump 345b activates with the valve 346a being open, the cleanser is pumped out of the cleanser tank 323c into the cleaning-water tank 321 as indicated by an arrow Y61b. After that, as the pump 342b activates, the cleanser flows from the cleaning-water tank 321 to each of the cleaning-water flow-path constituents as indicated by an arrow Y64 and thus the cleaning process is performed. It is noted that, in the case shown in FIG. 8, it is possible to prepare a cleanser Ls1 having a concentration appropriate for cleaning the inside of the cleaning-water tank and the insides of the cleaning-water flow-path constituents by opening, under the control of the control unit 4, both the valve 346a and the valve 341a of the pipe 341 that is connected to the cleaning-water supply source and thereby diluting the cleanser Ls contained in the attached cleanser tank 323c. In this case, if it is required to change the concentration of the cleanser Ls to appropriately clean the inside of the cleaning-water tank and the insides of the cleaning-water flow-path constituents because, for example, contents of the cleanser is changed, the analyzer has conducted an analysis for a specific analysis item, or an analysis of a particular sample needs an increase of the cleaning effect, the control unit 4 prepares the cleanser Ls1 having the target concentration inside the analyzer by adjusting the open time of the valve 346a and the valve 341a.

As shown in FIG. 2, the pipe 347 that is bifurcated from the pipe 345 is provided and the cleanser Ls is sent into each of the tubes 234 via the tubes 354 that are connected to the pipe 347. However, as shown in FIG. 9, it is allowable to clean the tubes 234 using the cleanser Ls that is contained in the cleaning-water tank 321.

Figure 9:
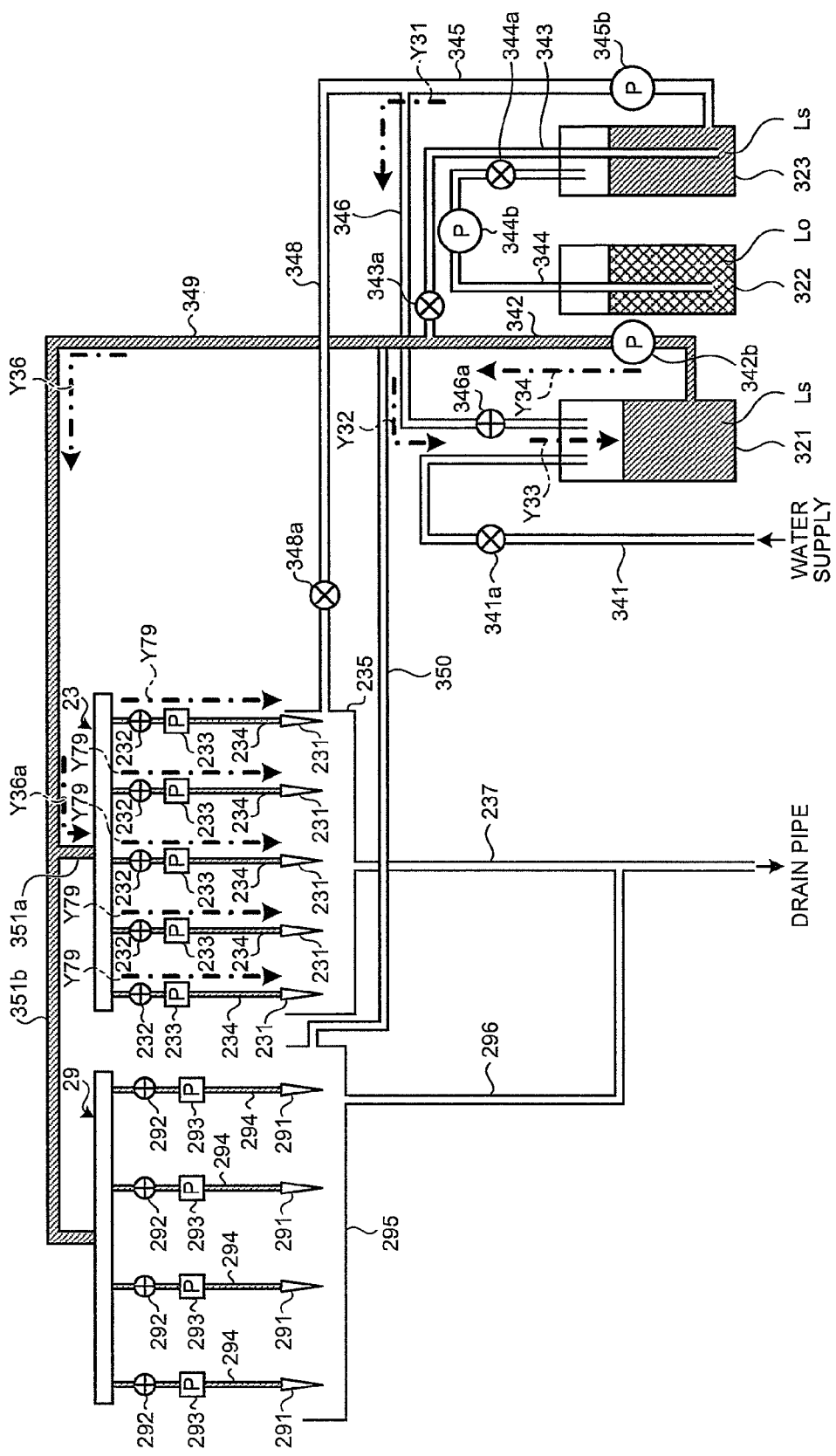
FIG. 9 is a schematic diagram that explains another cleaning system for cleaning, inside the device, a sample to be analyzed by the analyzer shown in FIG. 1 or a member that has been in contact with the liquid that is used for the analysis process.

More specifically, as shown in FIG. 9, the control unit 4 opens the valve 346a and activates the pump 345b, thereby sending the cleanser Ls from the cleanser tank 323 into the cleaning-water tank 321 as indicated by the arrows Y31 to Y33. After that, the control unit 4 activates the pump 342b with the valves 232 of the diluted-sample dispensing unit 23 being open, thereby causing the cleanser Ls to flow from the cleaning-water tank 321 to the diluted-sample dispensing unit 23 as indicated by the arrows Y34, Y36, and Y36a. The control unit 4 then activates the syringe pumps 233 so that the cleanser Ls is supplied to each of the tubes 234 as indicated by an arrow Y79 and thus the cleaning process is performed. With this configuration, the pipe 347, the valves 352, and the tubes 354 that are provided in the example shown in FIG. 2 to clean each of the tubes 234 are not needed.

Although the analyzer that conducts immunological tests is used in the present embodiment, some other analyzers that conduct biochemical tests or blood transfusion tests can be used. A case of an analyzer that conducts biochemical tests is described below with reference to FIGS. 10 and 11.

Figure 10:
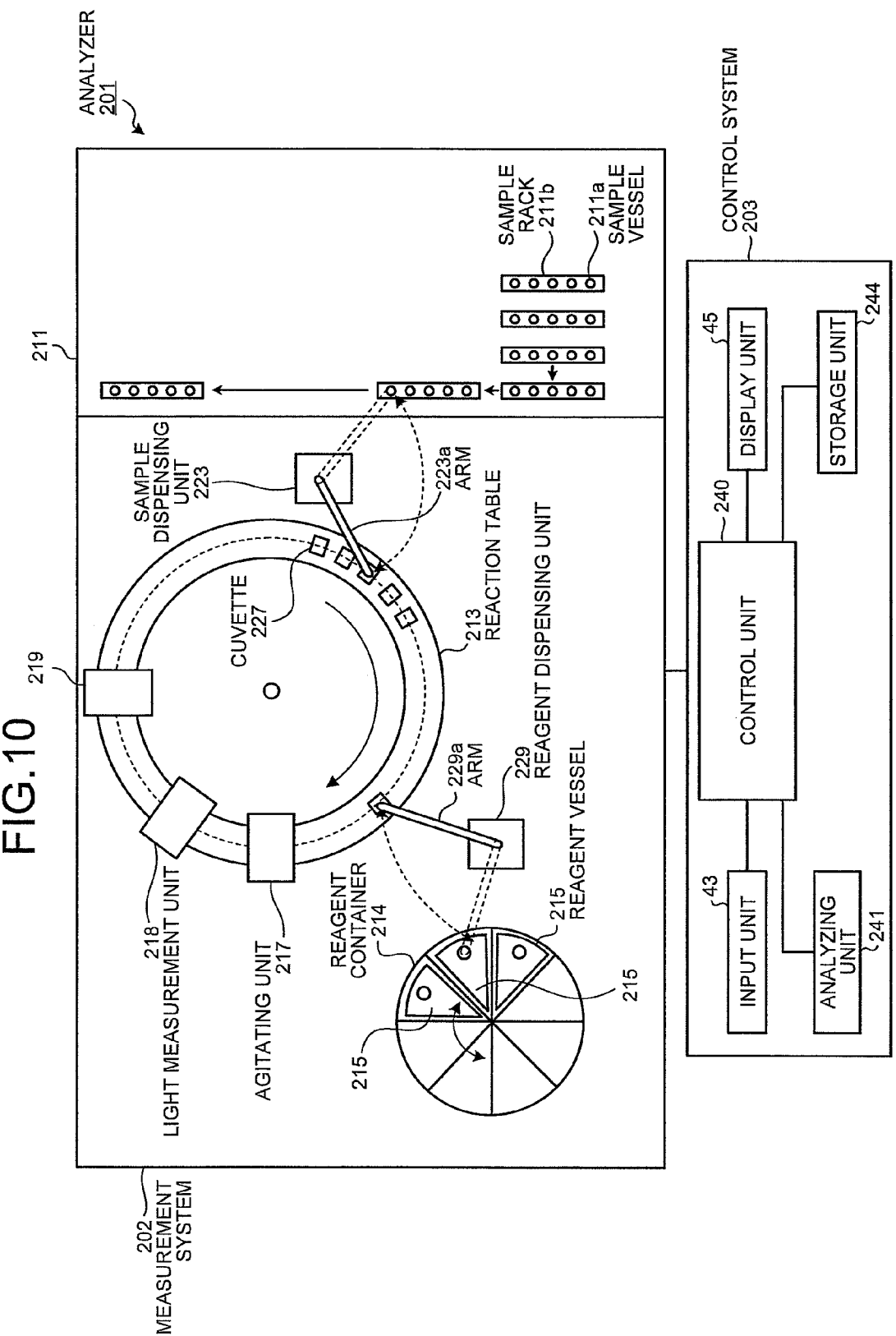
FIG. 10 is a schematic diagram of the configuration of an analyzer according to another embodiment.
Figure 11:
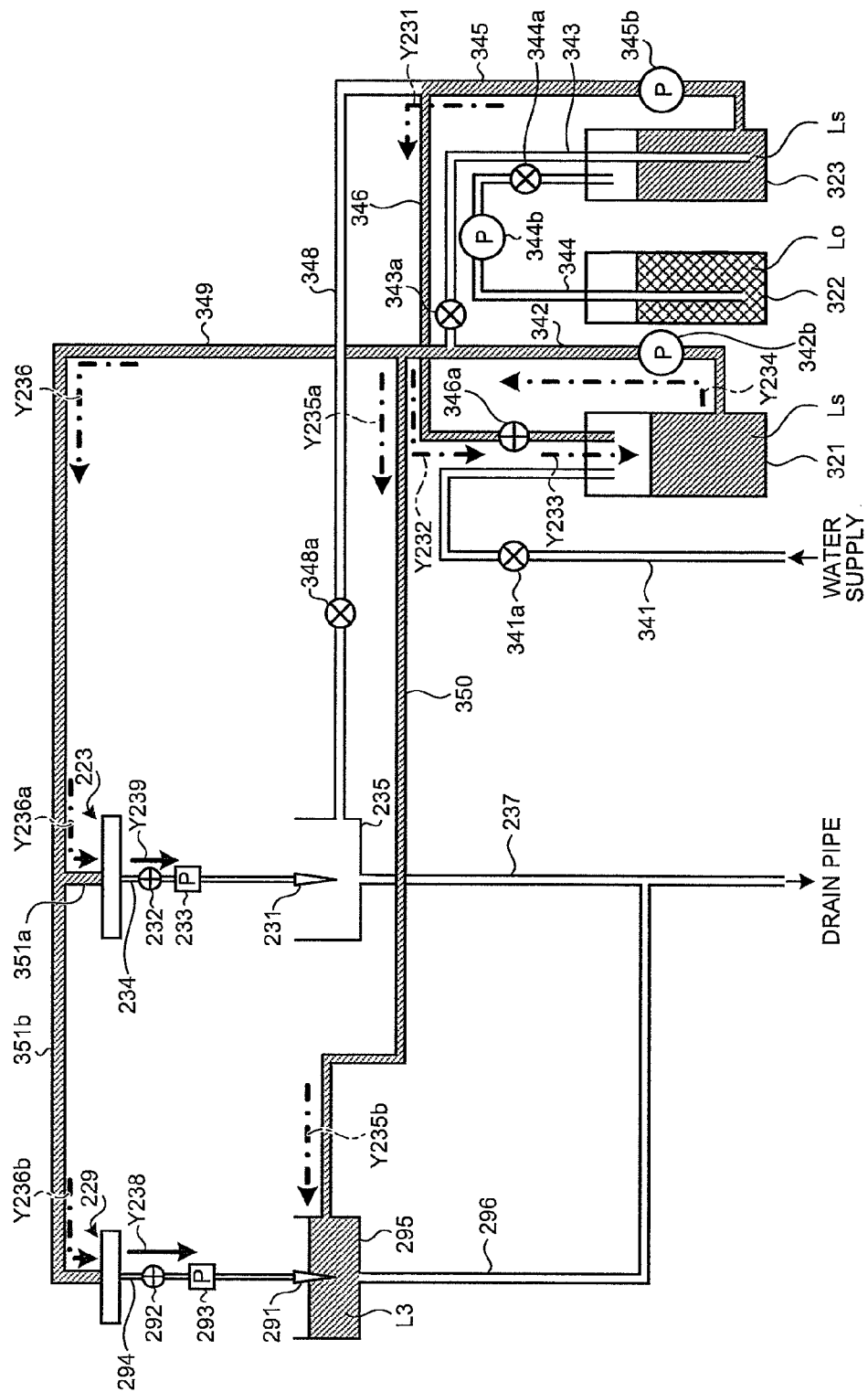
FIG. 11 is a schematic diagram that explains a cleaning system for cleaning, inside the device, a sample to be analyzed by the analyzer shown in FIG. 10 or a member that has been in contact with liquid that is used for an analysis process.

As shown in FIGS. 10 and 11, an analyzer 201 that conducts biological tests includes, as a measurement system 202, a sample-rack conveying unit 211 that sequentially conveys a plurality of sample racks 211b on which a plurality of sample vessels 211a each containing a liquid sample, such as blood or urine, are mounted in the direction indicated by the arrows shown in the figure; a sample dispensing unit 223 that is connected to the syringe pump 233 and provided with the sample nozzle 231 at an end of an arm 223a to suck and discharge a sample; a reaction table 213 that conveys a cuvette 227 to target positions including a position to dispense a sample or a reagent, a position to agitate the cuvette 227, a position to measure the cuvette 227 using light, and a position to clean the cuvette 227; a reagent container 214 that can contain a plurality of reagent vessels 215 that contains reagents to be dispensed into the cuvettes 227; a reagent dispensing unit 229 that is connected to the syringe pump 293 and provided with the reagent nozzle 291 at an end of an arm 229a to suck and discharge the reagents; an agitating unit 217 that agitates the sample and the reagent in the cuvette 227; a light measurement unit 218 that measures optical properties of the liquid contained in the cuvette 227; and a cleaning unit 219 that cleans the cuvette 227 after the measurement by the light measurement unit 218.

The analyzer 201 includes, as a control system 203, a control unit 240 that controls processes and operations of the units of the analyzer 201; the input unit 43; an analyzing unit 241 that analyzes the sample using a measurement result that is obtained by the light measurement unit 218; a storage unit 244 that stores therein various data including an analysis result of the sample; and the display unit 45.

The analyzer 201 performs the process of cleaning the inside of the cleaning-water tank 321 and the insides of the cleaning-water flow-path constituents by performing the processes shown in FIG. 3 in the same manner as the analyzer 1 performs. The control unit 240 performs the process of supplying the cleanser to the cleaning-water tank 321 shown in FIG. 3 (Step S4), more particularly, sends the cleanser Ls from the cleanser tank 323 into the cleaning-water tank 321 via the pipes 345 and 346 as indicated by arrows Y231, Y232, and Y233.

The control unit 240 performs the process of cleaning the cleaning-water flow-path constituents shown in FIG. 3, more particularly, activates the pump 342b with the valve 346a being open so that the cleanser Ls flows from the cleaning-water tank 321 into the pipe 342 as indicated by an arrow Y234. The cleanser Ls, which is contained in the cleaning-water tank 321, is sent to the pipe 350 and the reagent-nozzle cleaning tank 295 as indicated by arrows Y235a and Y235b. After that, the cleanser Ls, which is contained in the cleaning-water tank 321, flows from the pipe 342 to the pipes 349, 351a, and 351b as indicated by arrows Y236, Y236a, and Y236b and flows, if the valves 232 and 292 open under the control of the control unit 4, into the tubes 294 and 234 as indicated by arrows Y238 and Y239. The control unit 240 then performs the process the same as the rinse process shown in FIG. 3 so that the insides of the cleaning-water tank 321 and the cleaning-water flow-path constituents are rinsed using the cleaning water Lw.

As mentioned above, if an analyzer that conducts biochemical tests includes the connection pipe 346 that connects the cleanser tank 323 with the cleaning-water tank 321, opens the valve 346a provided to the connection pipe 346, and activates the pump 345b provided to the pipe 345 to which the connection pipe 346 is connected, it is easy to clean the inside of the cleaning-water tank 321 and the insides of the cleaning-water flow-path constituents.

The analyzers 1 and 201 that are described in the above embodiments can be implemented by executing a predetermined program using a computer system. The computer system implements the processes performed by the analyzer by reading a program from a predetermined recording medium and executing the read program. The predetermined recording medium includes any types of recording media that stores therein programs readable by the computer system including "portable physical media", such as a flexible disk (FD), a CD-ROM, an MO disk, a DVD, a magnet optical disk, and an IC card, and "communication media" that temporarily store therein the program for sending of the program, such as a hard disk drive (HDD) that is included in or excluded from the computer system. The computer system implements the operation of the analyzer by obtaining the program from a management server or another computer system that is connected to the computer system via a network line and executing the obtained program.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An analyzer that includes a cleaning system that cleans a specimen to be analyzed or a member that has been in contact with liquid used in an analysis process, the analyzer comprising:
   a cleanser tank that contains a cleanser;
   a cleaning-water tank that contains purified water including any one of, or combinations of, ion-exchange water, distilled water, and ultra-filtrated water;
   a connection pipe that connects the cleanser tank with the cleaning-water tank;
   a pump that is provided to the connection pipe and pumps the cleanser out of the cleanser tank to the cleaning-water tank;
   a valve that is provided to the connection pipe and adjusts a flow of the cleanser from the cleanser tank into the cleaning-water tank; and
   a control unit programmed to open the valve and cause the pump to pump the cleanser out of the cleanser tank to the cleaning-water tank via the connection pipe and programmed to cause the cleanser to further flow from the cleaning-water tank through cleaning-water flow-path constituents that form a flow path being separate from the connection pipe, so as to clean the inside of the cleaning-water tank and the insides of the cleaning-water flow-path constituents wherein the control unit is further programmed to cause the purified water including any one of, or combinations of, ion-exchange water, distilled water, and ultra-filtrated water, separate from the cleanser, to flow from the cleaning-water tank through the flow path so as to clean the specimen to be analyzed or the member that has been in contact with liquid used in the analysis process.

2. The analyzer according to claim 1, further comprising
   an input unit that receives information about an instruction to clean the inside of the cleaning-water tank and the insides of the cleaning-water flow-path constituents, wherein when the control unit receives the information about the instruction from the input unit, the control unit opens the valve and causes the pump to pump the cleanser out of the cleanser tank to the cleaning-water tank via the connection pipe.

3. The analyzer according to claim 1, wherein
   when a predetermined time period has elapsed after the last cleaning of the inside of the cleaning-water tank and the insides of the cleaning-water flow-path constituents,
   when the number of analysis requests received by the analyzer is a predetermined number or smaller, or
   when reaching a predetermined time set in advance as cleaning time at which the inside of the cleaning-water tank and the insides of the cleaning-water flow-path constituents are to be cleaned,
   the control unit opens the valve and causes the pump to pump the cleanser out of the cleanser tank to the cleaning-water tank via the connection pipe.

* * * * *